(12) United States Patent
Sonderegger

(10) Patent No.: US 11,260,173 B2
(45) Date of Patent: Mar. 1, 2022

(54) NEEDLE ASSEMBLY FOR SUBCUTANEOUS INFUSION SET

(71) Applicant: Becton, Dickinson and Company, Franklin Lakes, NJ (US)

(72) Inventor: Ralph Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 368 days.

(21) Appl. No.: 16/329,616

(22) PCT Filed: Sep. 14, 2017

(86) PCT No.: PCT/US2017/051589
§ 371 (c)(1),
(2) Date: Feb. 28, 2019

(87) PCT Pub. No.: WO2018/053147
PCT Pub. Date: Mar. 22, 2018

(65) Prior Publication Data
US 2019/0224409 A1    Jul. 25, 2019

Related U.S. Application Data

(60) Provisional application No. 62/395,197, filed on Sep. 15, 2016.

(51) Int. Cl.
*A61M 5/158* (2006.01)
*A61M 5/32* (2006.01)

(52) U.S. Cl.
CPC .............. *A61M 5/158* (2013.01); *A61M 5/32* (2013.01); *A61M 5/3243* (2013.01);
(Continued)

(58) Field of Classification Search
CPC ...... A61M 5/158; A61M 5/1626; A61M 5/32; A61M 5/3205; A61M 5/3206;
(Continued)

(56) References Cited

U.S. PATENT DOCUMENTS

| 4,747,831 A | * | 5/1988 | Kulli ................. A61M 25/0631 604/110 |
| 5,575,777 A | * | 11/1996 | Cover ............... A61M 25/0606 604/110 |

(Continued)

FOREIGN PATENT DOCUMENTS

| EP | 2796160 A1 | 10/2014 |
| EP | 2902054 A1 | 8/2015 |

(Continued)

*Primary Examiner* — Kami A Bosworth
(74) *Attorney, Agent, or Firm* — Dickinson Wright PLLC

(57) ABSTRACT

A needle assembly including a needle having a sharpened end and an opposing end and a needle tip shield for shielding the needle. The needle tip shield includes a needle shield connectable to a base and a needle hub fixedly connected to the opposing end. The needle shield and needle hub displace relative to each other from a first state, in which the sharpened end of the needle is exposed outside the needle shield, to a second state, in which the sharpened end of the needle is shielded by the needle shield. An actuation button is movably connected to the needle hub to maintain the needle shield and needle hub in a releasable locked state in a first button position relative to the needle hub and to permit the needle shield and needle hub to displace relative to each other in a second button position relative to the needle hub.

16 Claims, 15 Drawing Sheets

(52) U.S. Cl.
CPC ............ *A61M 2005/1585* (2013.01); *A61M 2005/1587* (2013.01); *A61M 2005/3247* (2013.01); *A61M 2005/3267* (2013.01)

(58) Field of Classification Search
CPC .... A61M 5/321; A61M 5/322; A61M 5/3221; A61M 5/3232; A61M 2005/1583; A61M 2005/1585; A61M 2005/1586; A61M 2005/1587; A61M 2005/3228; A61M 2005/3236; A61M 5/3243; A61M 2005/3247; A61M 2005/3267; A61M 2205/581; A61B 5/15144; A61B 5/15192; A61B 5/15194; A61B 5/15196
See application file for complete search history.

(56) References Cited

U.S. PATENT DOCUMENTS

| | | | | |
|---|---|---|---|---|
| 5,769,826 | A | * | 6/1998 | Johnson .............. A61M 5/3232 600/576 |
| 5,885,257 | A | * | 3/1999 | Badger .............. A61M 5/3232 604/195 |
| 5,935,113 | A | * | 8/1999 | Dysarz ................. A61M 5/322 604/263 |
| 6,039,713 | A | * | 3/2000 | Botich ................ A61M 5/2429 604/110 |
| 6,090,078 | A | * | 7/2000 | Erskine ............ A61M 25/0631 128/919 |
| 6,123,688 | A | * | 9/2000 | Botich .................... A61M 5/24 604/110 |
| 6,641,555 | B1 | * | 11/2003 | Botich .................. A61M 5/158 604/110 |
| 2002/0068907 | A1 | * | 6/2002 | Dysarz ............... A61M 5/3232 604/191 |
| 2003/0078540 | A1 | | 4/2003 | Saulenas et al. |
| 2003/0120222 | A1 | * | 6/2003 | Vaillancourt ..... A61M 25/0643 604/263 |
| 2004/0158207 | A1 | | 8/2004 | Hunn et al. |
| 2007/0255221 | A1 | * | 11/2007 | Nakajima ......... A61M 25/0631 604/168.01 |
| 2009/0259178 | A1 | | 10/2009 | Brechbuehler et al. |
| 2010/0004597 | A1 | | 1/2010 | Gyrn et al. |
| 2011/0178473 | A1 | * | 7/2011 | Richards ............. A61M 5/3257 604/198 |
| 2013/0237918 | A1 | | 9/2013 | Gyrn et al. |
| 2013/0338598 | A1 | | 12/2013 | Gyrn et al. |
| 2014/0088509 | A1 | | 3/2014 | Sonderegger et al. |
| 2014/0316379 | A1 | | 10/2014 | Sonderegger et al. |

FOREIGN PATENT DOCUMENTS

| | | |
|---|---|---|
| JP | H09504190 A | 4/1997 |
| JP | 2004524926 | 8/2004 |
| JP | 2015500101 | 1/2015 |
| WO | WO-2013086463 A1 | 6/2013 |
| WO | WO-2015161294 A1 | 10/2015 |

* cited by examiner

NEEDLE ASSEMBLY FOR SUBCUTANEOUS INFUSION SET

This application claims priority under 35 U.S.C. § 119(e) from U.S. Provisional Application Ser. No. 62/395,197, filed on Sep. 15, 2016, which is incorporated herein by reference in its entirety.

FIELD OF THE INVENTION

The present invention relates to safety modules, and more particularly, to safety modules with automatic needle retraction.

BACKGROUND OF THE INVENTION

Needle sharps safety is a growing and important aspect of medical devices. Regulatory and market forces have both driven the need for a reliable way of protecting health-care professionals, custodial personnel and users from needle stick injury. The ability to protect users and personnel from needle stick injury is a critical aspect that influences the market success of a medical device.

The introduction of fluids into a patient using a catheter and insertion device is known. For intravenous infusion, a common insertion device is an introducer needle received in a catheter. Currently there are several devices that prevent needle stick injury and enable the safe disposal of an introducer needle. These devices are often complicated, expensive and/or difficult to manufacture. Additionally, some previous devices have shown actuation inconsistencies throughout their operating window.

As such, it may be appreciated that there is a continuing need for a new and improved safety module for an insertion needle that addresses the problems noted above and is simple and low-cost to manufacture. Embodiments of the present invention substantially fulfill this need.

SUMMARY OF THE INVENTION

In accordance with an aspect of the present invention, a needle assembly comprises a needle having a sharpened end and an opposing end, and a needle tip shield for shielding the needle. The needle tip shield comprises a needle shield connectable to a base, and a needle hub fixedly connected to the opposing end of the needle. The needle shield and needle hub are displaceable relative to each other from a first state in which the sharpened end of the needle is exposed outside the needle shield, to a second state in which the sharpened end of the needle is shielded by the needle shield. The needle tip shield also includes an actuation button movably connected to the needle hub to maintain the needle shield and needle hub in a releasable locked state in a first button position relative to the needle hub, and to permit the needle shield and needle hub to displace relative to each other in a second button position relative to the needle hub.

In accordance with another aspect of the present invention, a needle assembly comprises a needle having a sharpened end and an opposing end, the needle being insertable through a base, the base having a column extending proximally from the base and a head extending from the column forming an undercut between the base and the head. The needle assembly also includes a needle tip shield which comprises a needle hub releasably engaged with the base, the needle hub being fixedly connected to the opposing end of the needle and having an inner recess; an actuation button disposed on an outer wall of the needle hub; a needle shield, having a distal shield aperture, movably disposed in the inner recess, wherein in a first state of the needle shield relative to the needle hub, in which the sharpened end of the needle is exposed outside the needle shield, the actuation button extends through a distal aperture on the needle shield and engages the undercut on the base to releasably lock the needle shield and needle hub together and releasably engage the needle shield and the needle hub with the base; and a biasing element biasing the needle hub and the needle shield axially apart. Displacement of the actuation member relative to the needle hub releases the needle hub and needle shield from the base and releases the biasing element, and the needle shield displaces relative to the needle hub to cover the sharpened end of the needle.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
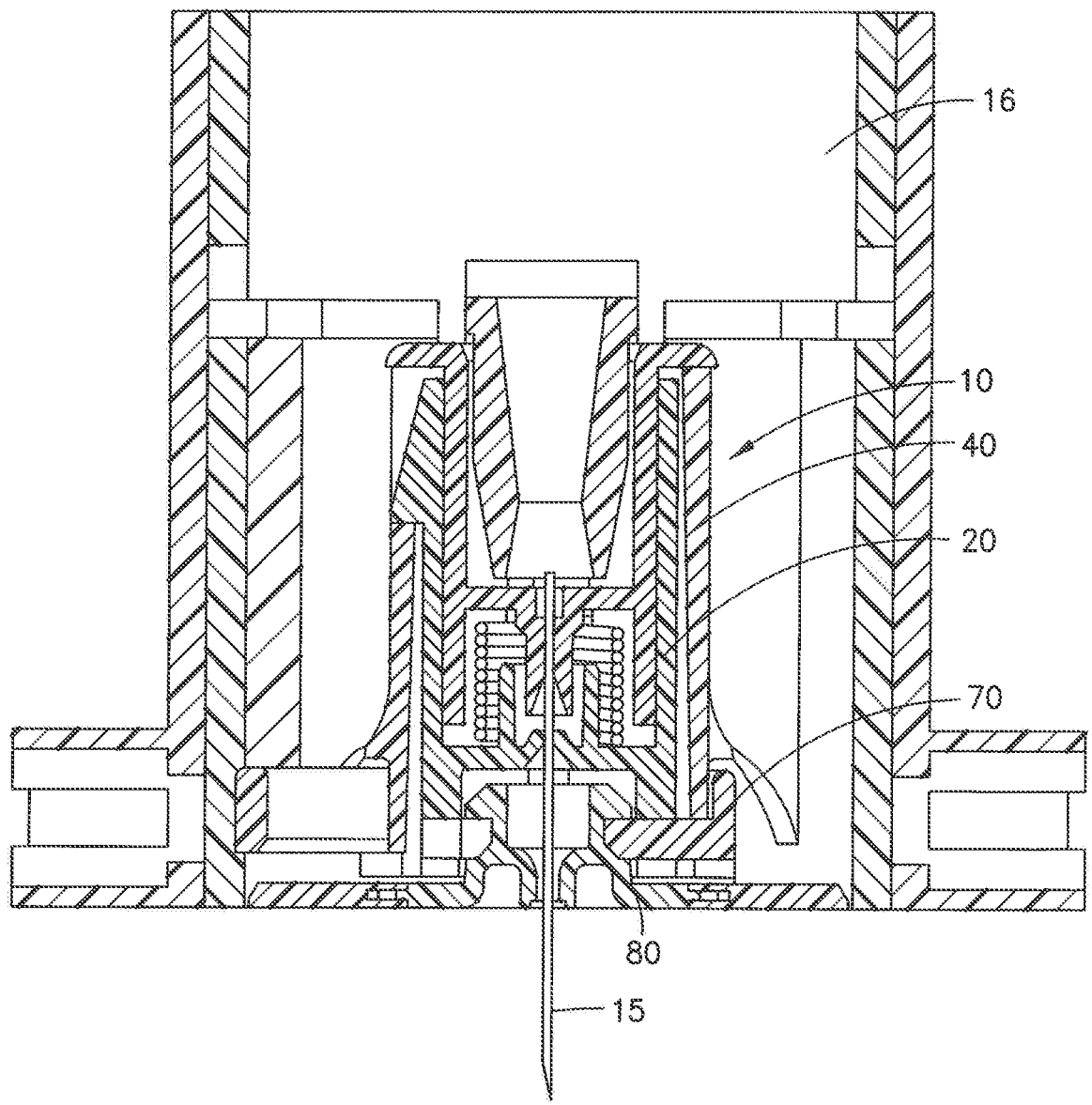
FIG. 1 is a cross-sectional view of a needle tip shield for an insertion needle, an infusion set base and an insertion device in accordance with an embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

FIG. 1 illustrates an exemplary embodiment of an infusion set assembly incorporating a needle tip shield 10 in accordance with the present invention. The infusion set assembly includes an introducer needle hub 40, a spring 56 and a needle shield 20 engaged with an infusion set base 80 via an actuation button 70. The needle tip shield 10 is mounted in an insertion device 16.

Figure 2:
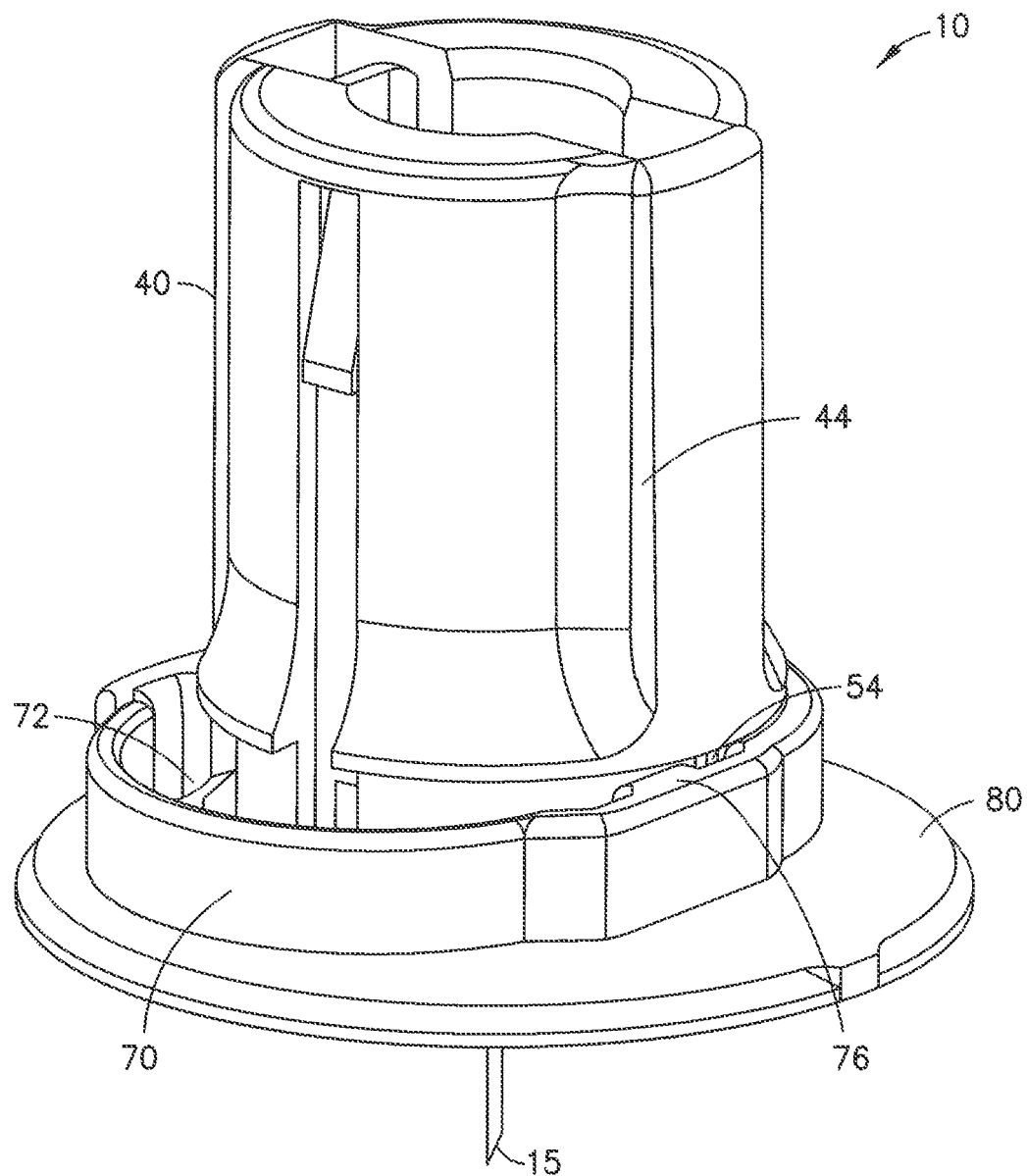
FIG. 2 is a perspective view of the needle tip shield and the base of FIG. 1.

FIG. 2 is a perspective view of the needle tip shield 10 engaged with the infusion set base 80 after being removed from the insertion device 16. As shown, the actuation button 70 is disposed on an outer wall 44 of the needle hub 40. In one exemplary embodiment, the needle hub 40 includes ratchet teeth 54 on the outer wall 44 that engage with a pawl structure 76 on an inner surface of the actuation button 70 to maintain the connection of the actuation button 70 with the needle hub 40.

Figure 3:
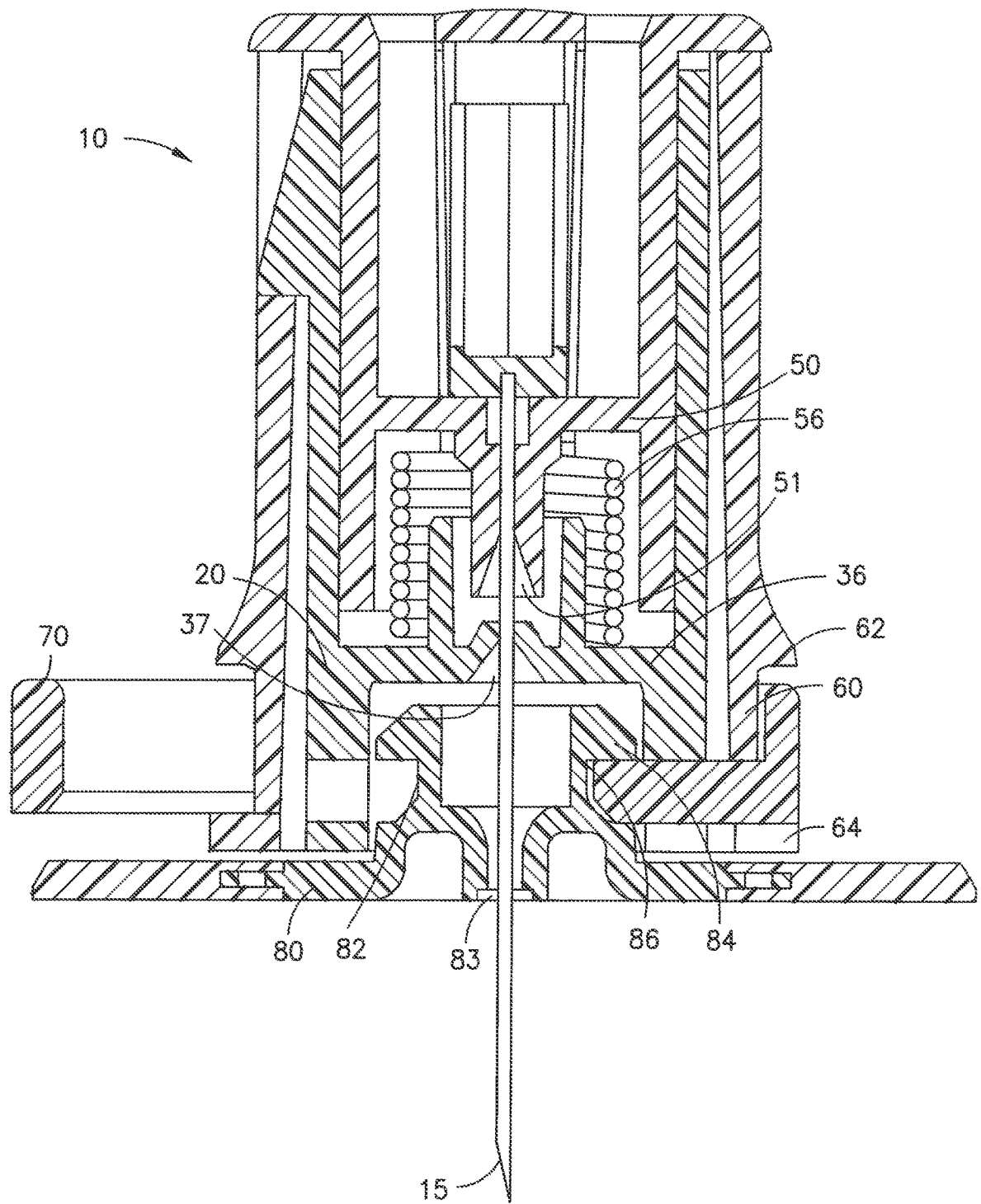
FIG. 3 is a cross-sectional view of the needle tip shield of FIG. 1 in a first operational state.

FIG. 3 further illustrates features of the needle tip shield 10 in a first loaded state prior to actuation of the actuation button 70 and removal of the needle tip shield 10 from the base 80. As shown, the base 80 includes a columnar post 82 surrounding an internal cavity 83. A head 84 is disposed at the proximal end of the post 82. The head 84 may be configured in a mushroom-shape.

Figure 5:
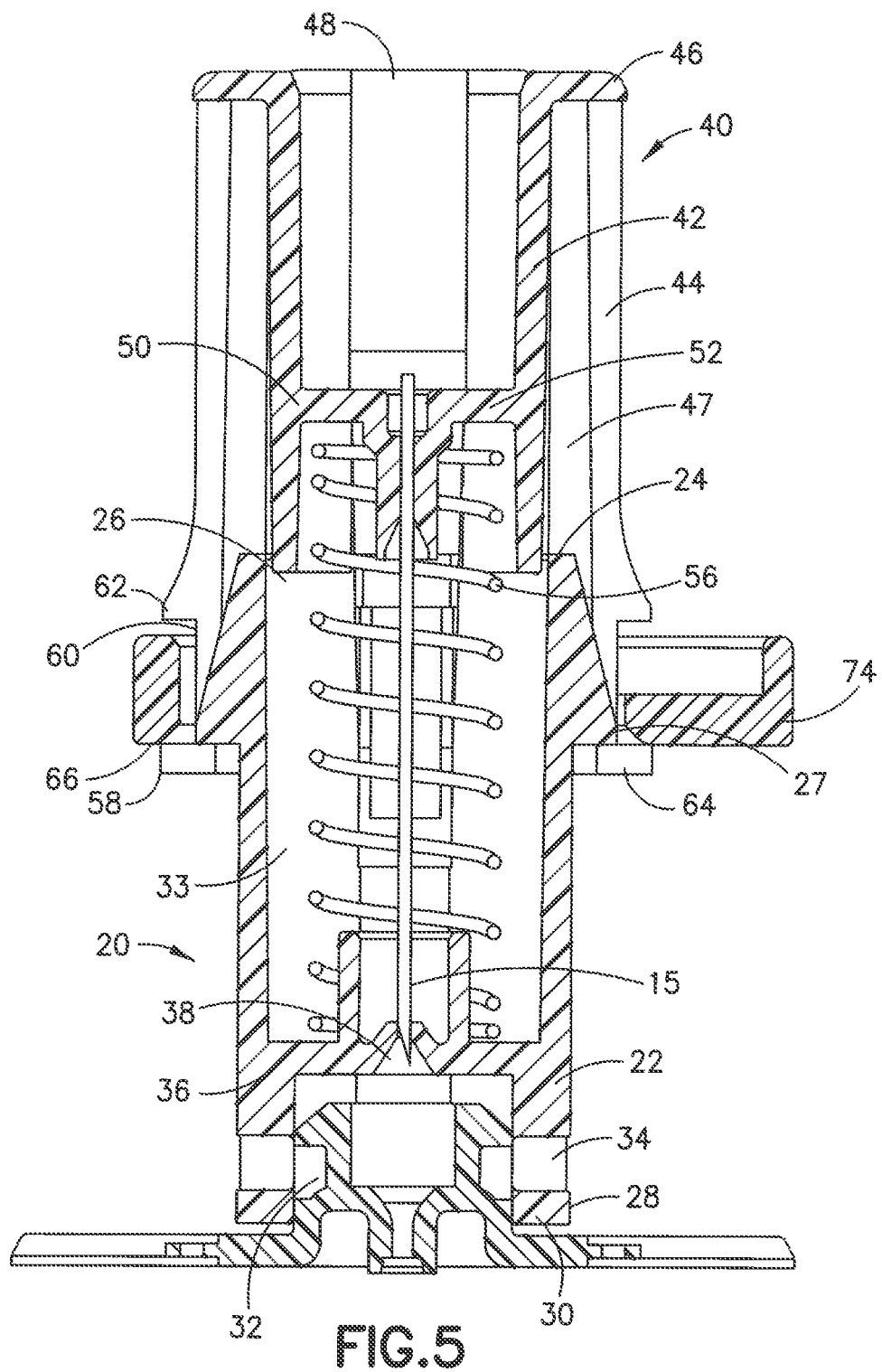
FIG. 5 is a cross-sectional view of the needle tip shield of FIG. 1 in a fully deployed state and the base of FIG. 1.

As shown in FIGS. 3 and 5, the needle shield 20 for selectively covering a distal end of a needle 15 includes a circumferential outer wall 22 with a proximal end 24 and a distal end 28. The proximal end 24 includes a proximal opening 26 and the distal end 28 includes a distal surface 30 with a distal opening 32 extending therethrough. A passageway 33 is formed by the outer wall 22 and extends between the proximal opening 26 and the distal opening 32. A transverse aperture 34 is formed in the outer wall 22 proximal to the distal surface 30. Additionally, proximal protrusions 27 are formed on the outer wall 22 at the proximal end 24 of the needle shield 20. The needle shield 20 also includes a shield shelf 36 extending radially inward in passageway 33, with an opening 37 for receiving the insertion needle 15.

The needle hub 40 can be movably disposed in the passageway 33 and along the outer wall 22 of the needle shield 20. The needle hub 40 includes a proximal end 46, a distal end 58 with an inner sidewall 42 and outer sidewall 44 extending therebetween. The inner sidewall 42 and outer sidewall 44 are connected at the proximal end 46 of the needle hub 40, and may be coaxial with a recess 47 formed therebetween. A hub shelf 50 extends radially inside of the inner sidewall 42 with an opening 51 for receiving the insertion needle 15. According to one embodiment, the insertion needle 15 is fixedly connected within the hub shelf 50. The needle hub outer sidewall 44 includes an aperture 60 proximal to the distal end 58. A hub flange 62 is disposed at an upper portion of the aperture 60 and a hub distal portion 64 is disposed at a lower portion of the aperture 60.

Referring back to FIG. 2, the actuation button 70 may have a circular shape defining an opening 72. The actuation button includes a latch 74 extending into the opening 72, and the latch 74 may be disposed on a lower portion of the actuation button 70 (see FIG. 3).

As illustrated in FIG. 3, the infusion set base 80 can be removably engaged with the actuation button 70 via an undercut 86 formed between the column 82 and the head 84. When the actuation button 70 is in a first, non-activated state, the latch 74 of the actuation button 70 is received in the distal aperture 60 of the needle hub 40, the distal aperture 34 of the needle shield 20 and in the undercut 86 of the infusion set base 80. In the first state the head 84 of the infusion set base 80 is received in the needle shield passage 33. The spring 56 is disposed between the hub shelf 50 and the needle shield shelf 36, and is compressed when the needle tip shield is in the first state shown in FIGS. 2 and 3.

Figure 4:
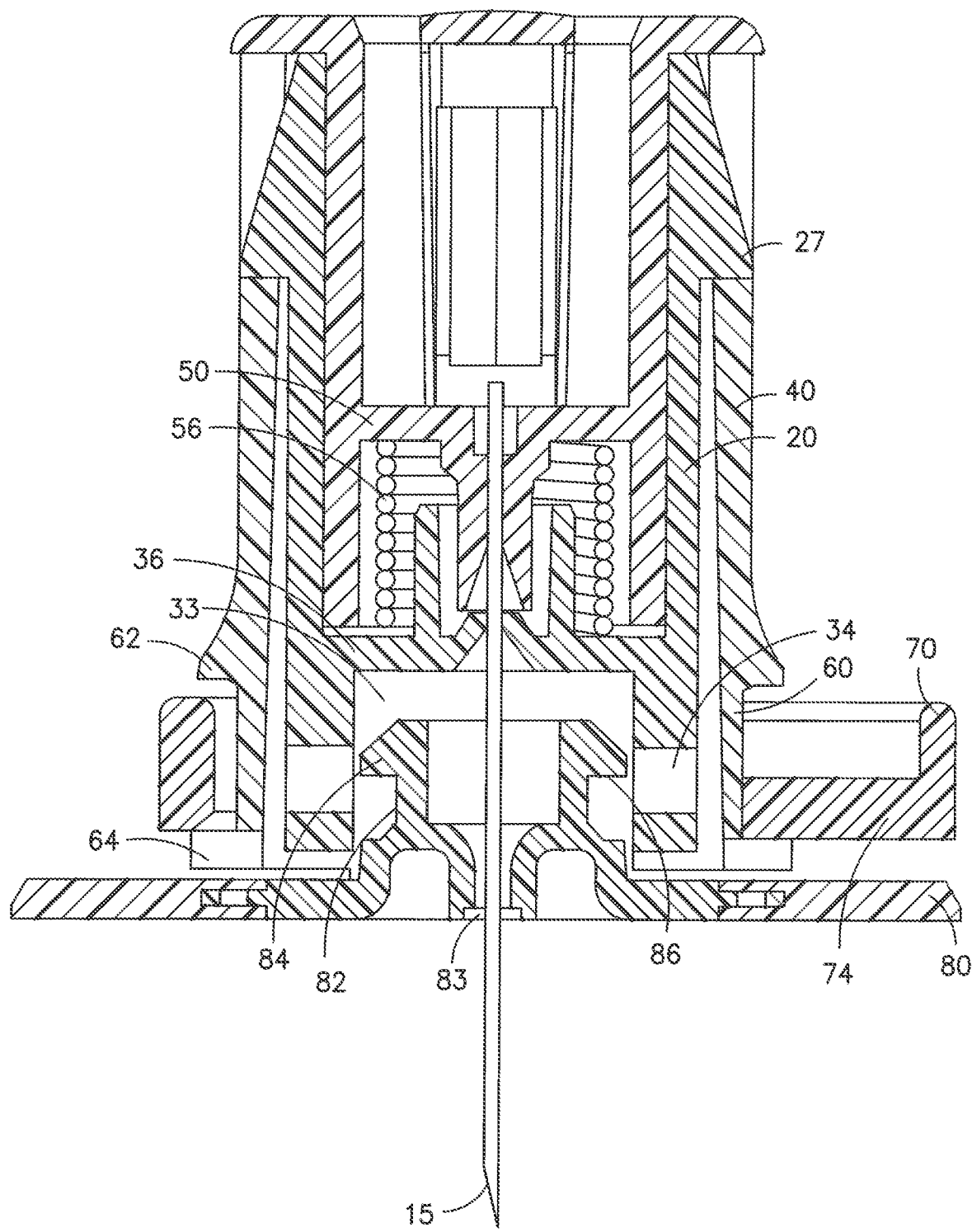
FIG. 4 is a cross-sectional view of the needle tip shield of FIG. 1 in a second operational state and the base of FIG. 1.

FIG. 4 illustrates that the actuation button 70 has moved to the right to unlock the needle shield 20 and needle hub 40 from the infusion set base 80. Preferably, the operational direction in which the activation button 70 moves in advancing from the first to the second state is perpendicular to the longitudinal axis of the needle hub 40. As shown in FIG. 5, when the activation button 70 is in the second state, the latch 74 of the actuation button 70 is disengaged from the undercut 86 of the infusion set base 80 and the distal aperture 34 of the needle shield 20. Engagement is maintained between the actuation button 70 and the outer wall 44 of the needle hub 40 by the ratchet teeth 54 on the outer wall 44 of the needle hub 40 and pawl structure 76 on the inner surface of the actuation button 70.

Once the latch 74 is removed from the distal aperture 34 of the needle shield 20, the spring displaces the needle hub 40 proximally relative to the needle shield 20. The needle shield 20 remains stationary relative to the base 80 (see FIG. 5).

Driven by the spring 56, the needle hub 40 and the needle shield 20 move apart from one another until the proximal protrusion 27 on the needle shield 20 engages an inner portion 66 of the distal portion 64 and a locking latch 29 disposed on the needle shield 20 passes the distal end of the needle hub and locks the needle hub 40 and needle shield 20 in a shielded state (see FIGS. 4-7). In the second state, the needle shield 20 can be removed from the head 84 of the infusion set base 80 (see FIG. 6).

Figure 6:
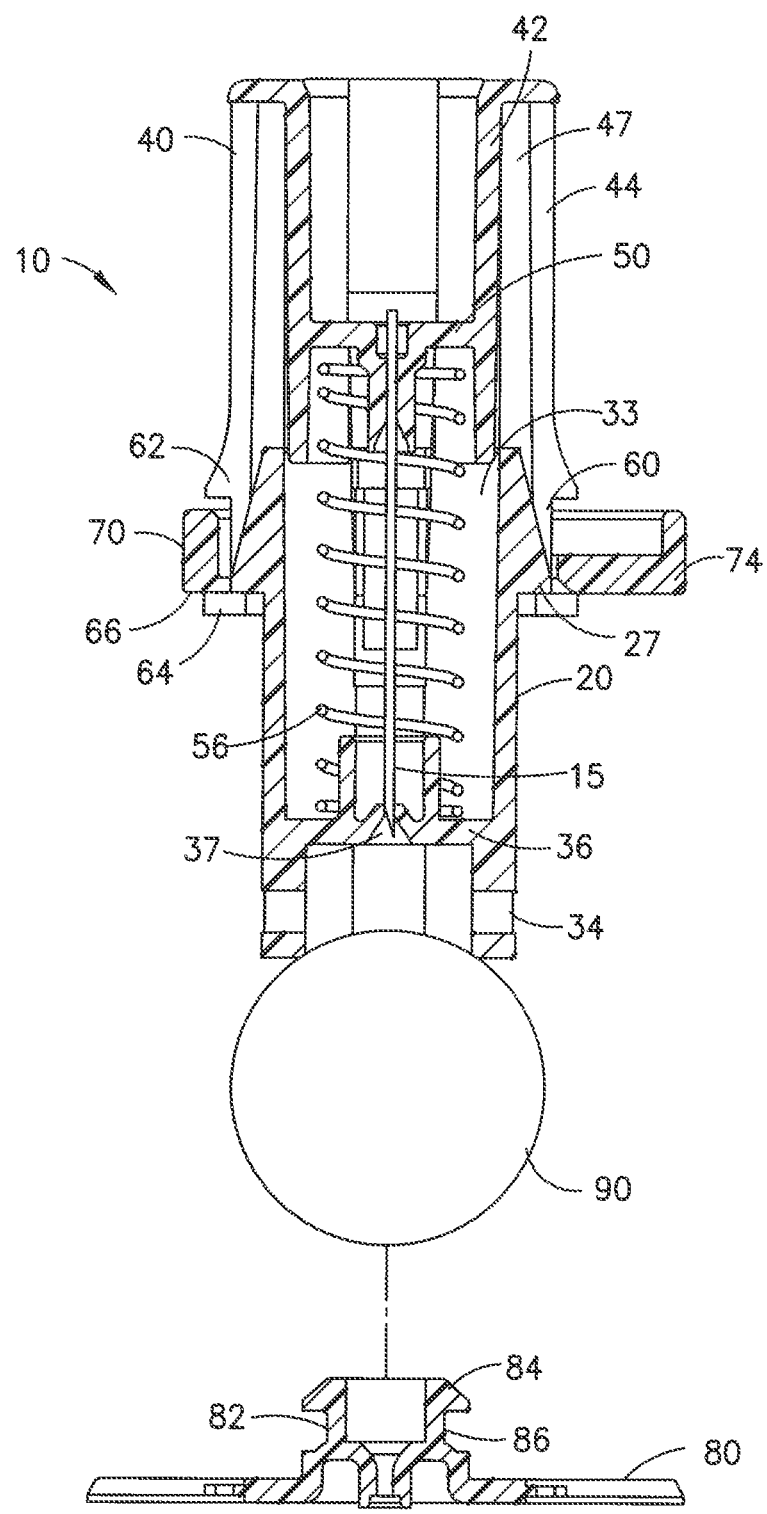
FIGS. 6-7 are cross-sectional views of the needle tip shield of FIG. 1 removed from the base of FIG. 1.
Figure 7:
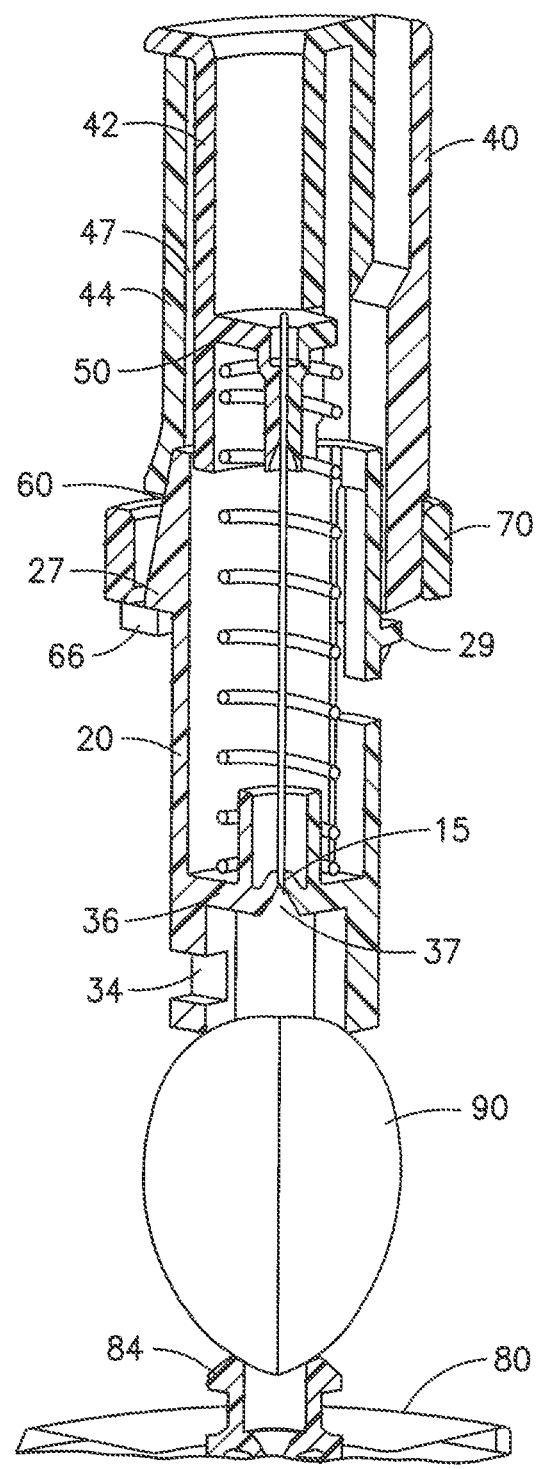

FIGS. 6 and 7 illustrate the fully deployed state in which the needle hub 40 has fully displaced and the needle tip shield 10 has been removed from the base 80. The introducer needle 15 is drawn into the needle shield opening 37. The needle shield 20 surrounds and conceals the introducer needle 15 so that an average finger, represented by sphere 90, will not fit through the distal opening 32 of the needle shield. Therefore, a user is provided with a mechanism to protect from an accidental needle stick.

Figure 8:
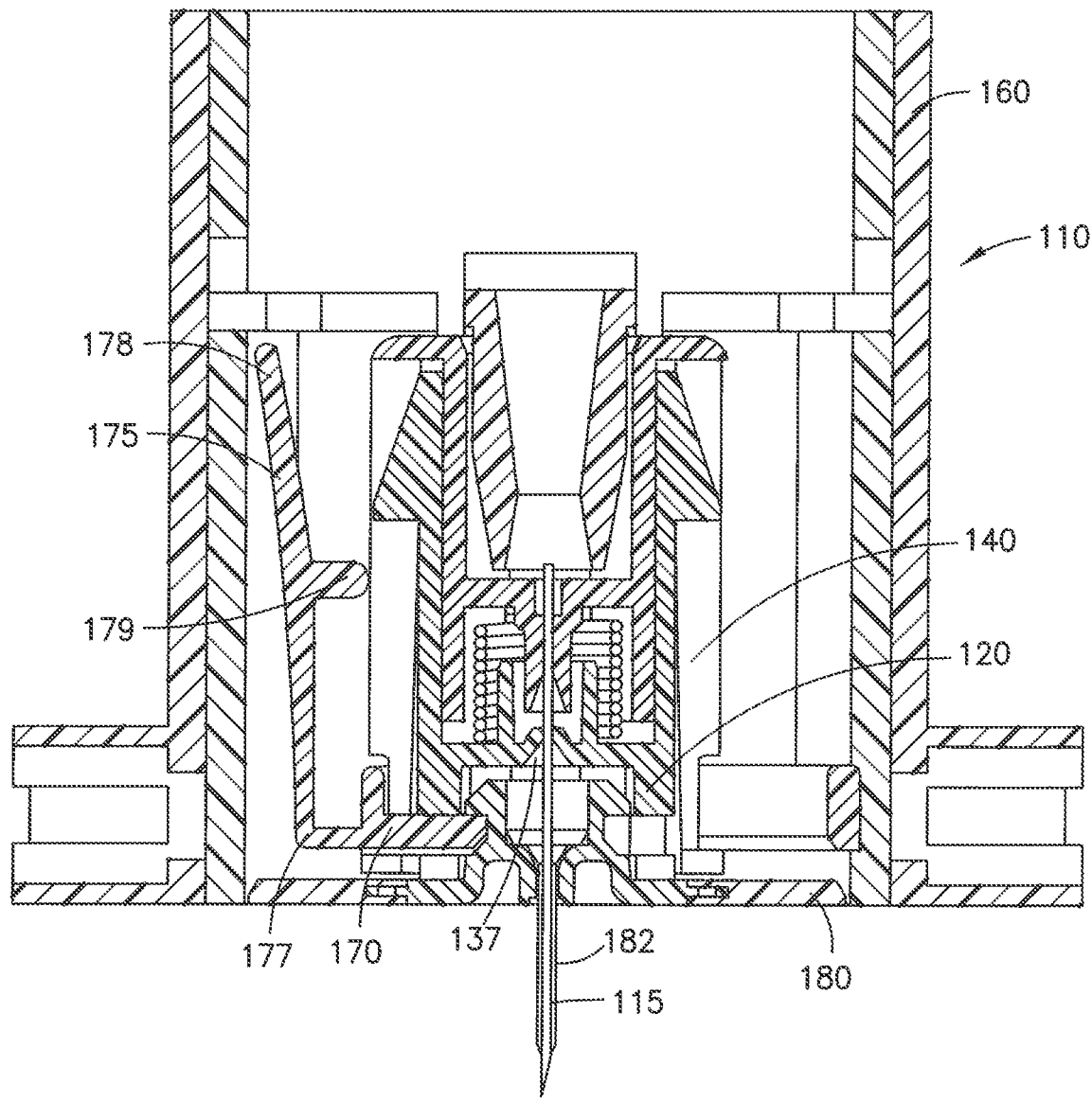
FIG. 8 is a cross-sectional view of a needle tip shield for an insertion needle, an infusion set base and an insertion device in accordance with another embodiment of the present invention.

FIG. 8 illustrates an alternative embodiment of the needle tip shield 110 in which the actuation button 170 includes a lever 175 including a push tab 178, a fulcrum 179 and a lower portion 177. As shown in FIG. 8, the needle tip shield 110 includes an introducer needle hub 140, a spring 156 and a needle shield 120 engaged with an infusion set base 180 via the actuation button 170. The introducer needle 115 passes through a flexible catheter 182 that extends from the infusion set base 180. The needle tip shield 110 is mounted in an insertion device 160.

Figure 9:
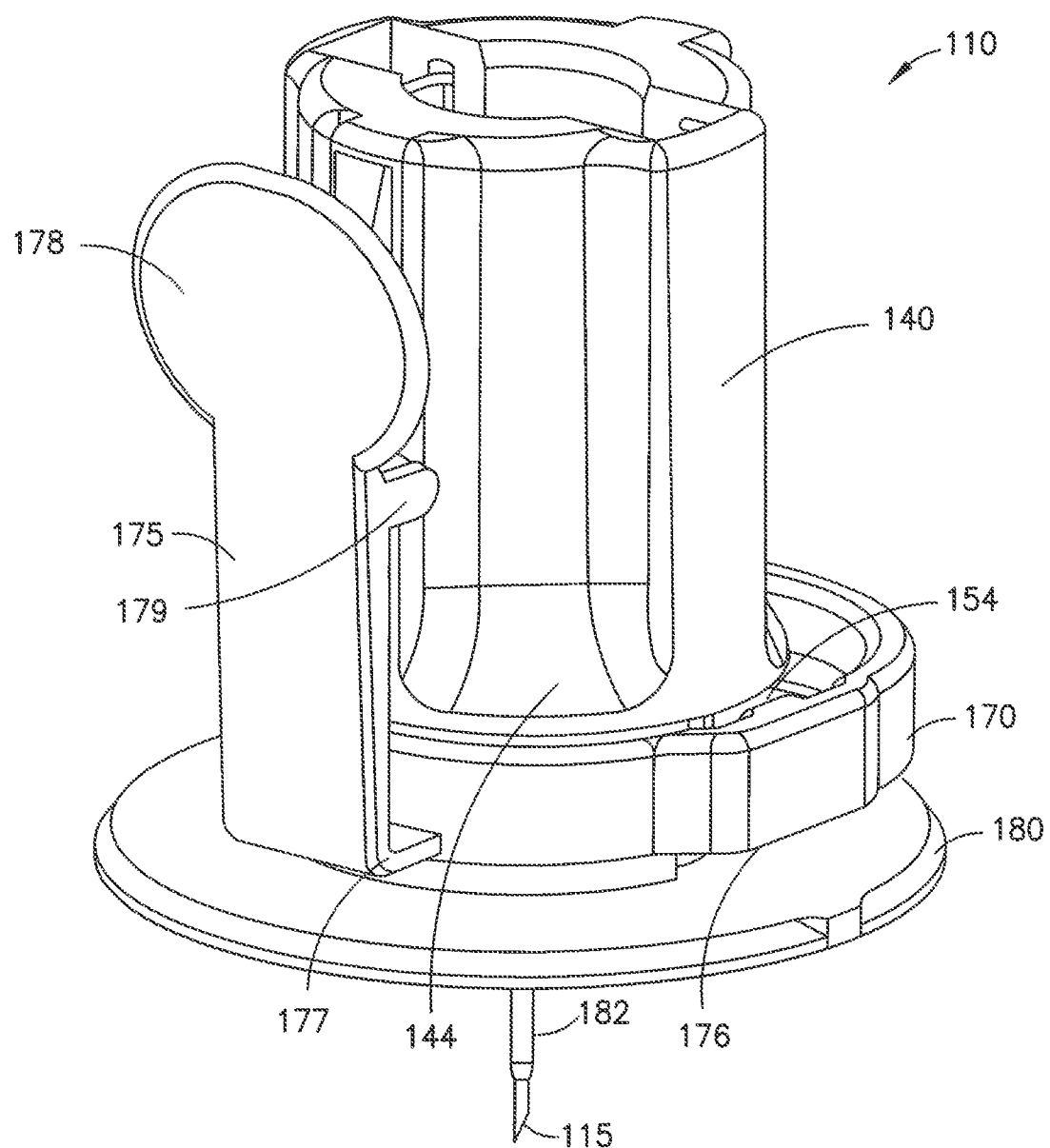
FIG. 9 is a perspective view of the needle tip shield and the base of FIG. 8 in a first operational state.

FIG. 9 is a perspective view of the needle tip shield 110 engaged with the infusion set base 180 after the insertion device 160 has been removed. The actuation button 170 is in a first state prior to actuation. As shown, the actuation button 170 is disposed on an outer wall 144 of the needle hub 170. In one exemplary embodiment, the needle hub 140 includes ratchet teeth 154 on the outer wall 144 that engages with a pawl structure 176 on an inner surface of the actuation button 170 to maintain the connection of the actuation button 170 with the needle hub 140.

Figure 10:
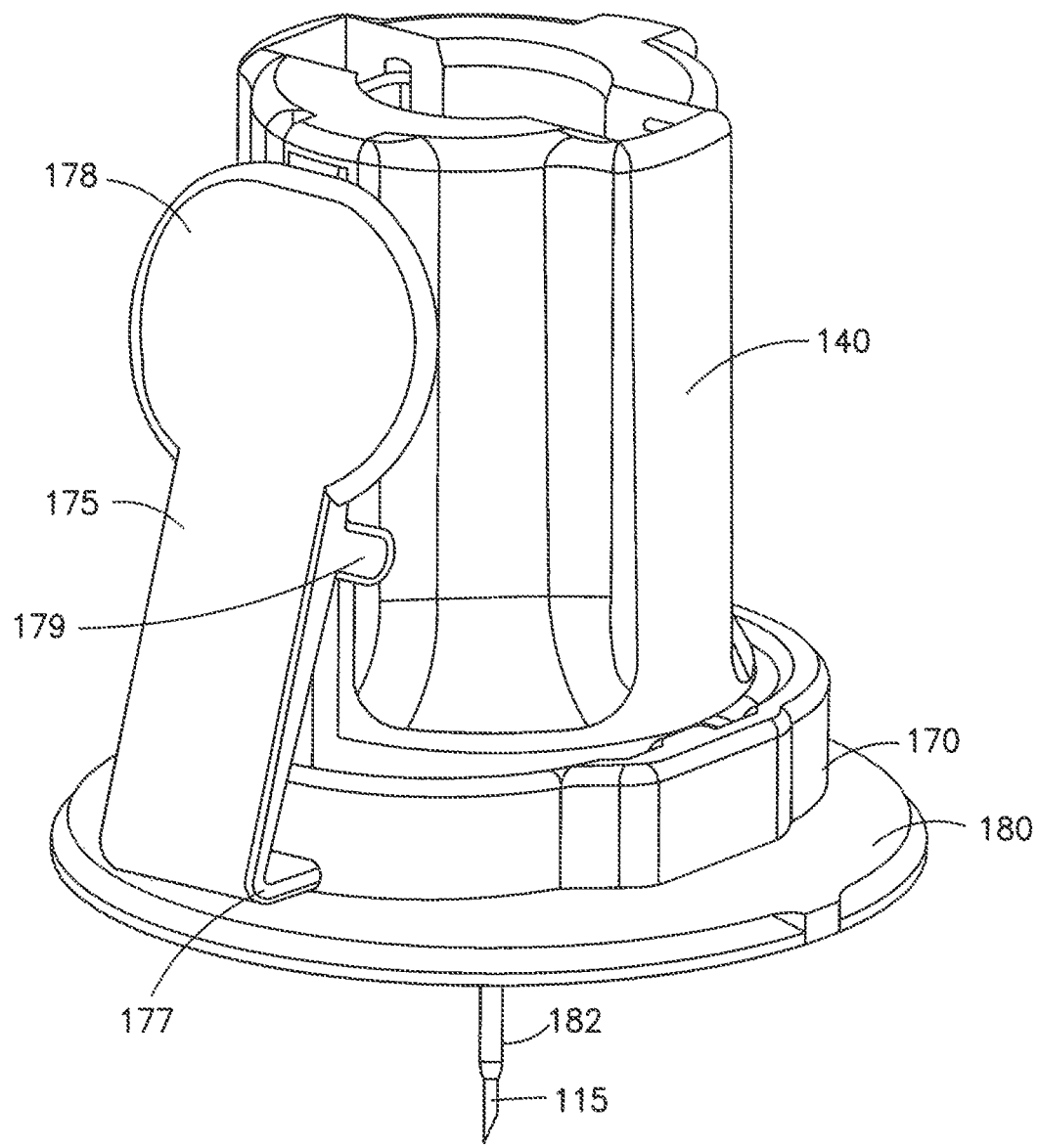
FIG. 10 is a perspective view of the needle tip shield and the base of FIG. 8 in a second operational state.
Figure 11:
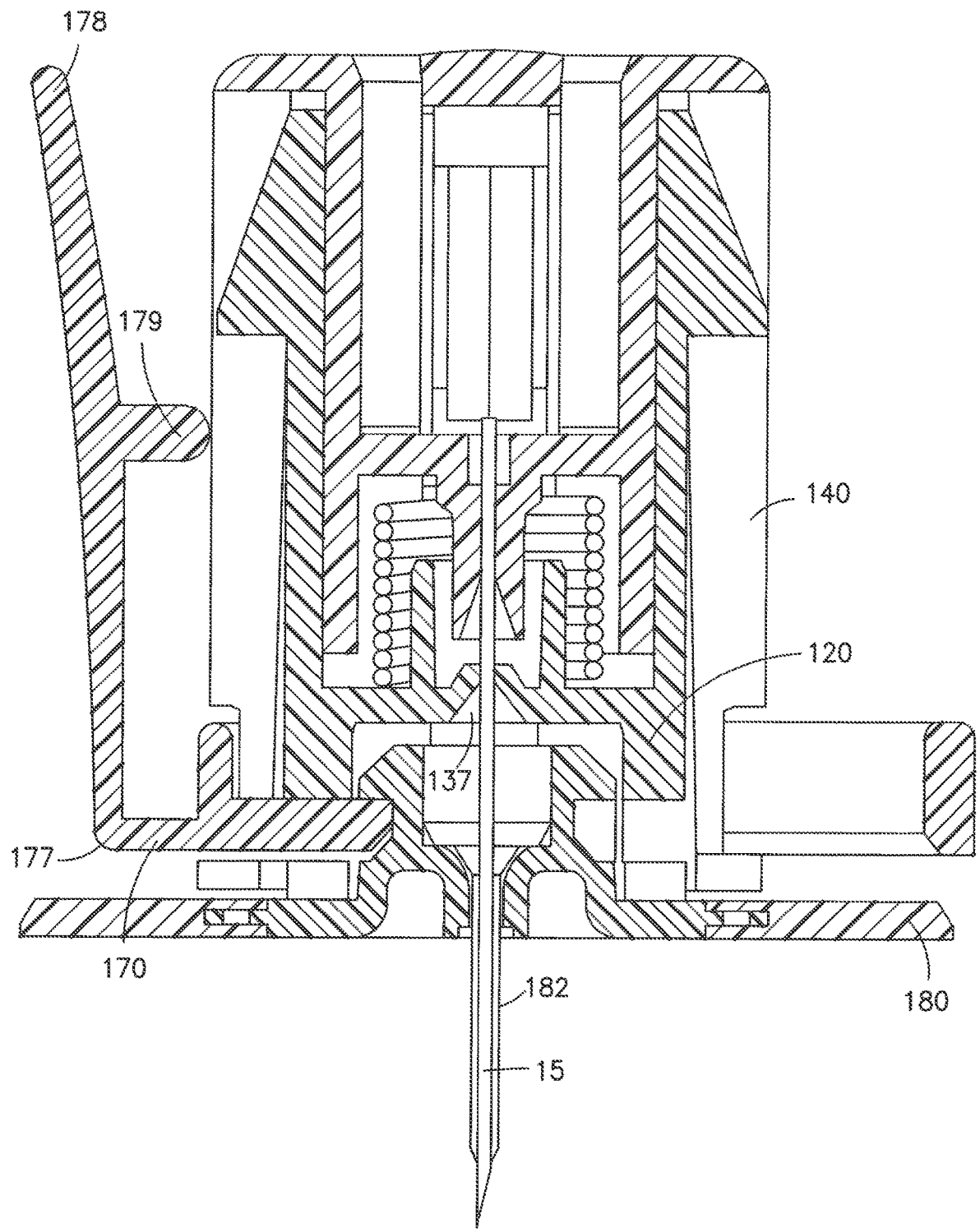
FIG. 11 is a cross-sectional view of the needle tip shield of FIG. 8 in the first operational state and the base of FIG. 8.
Figure 12:
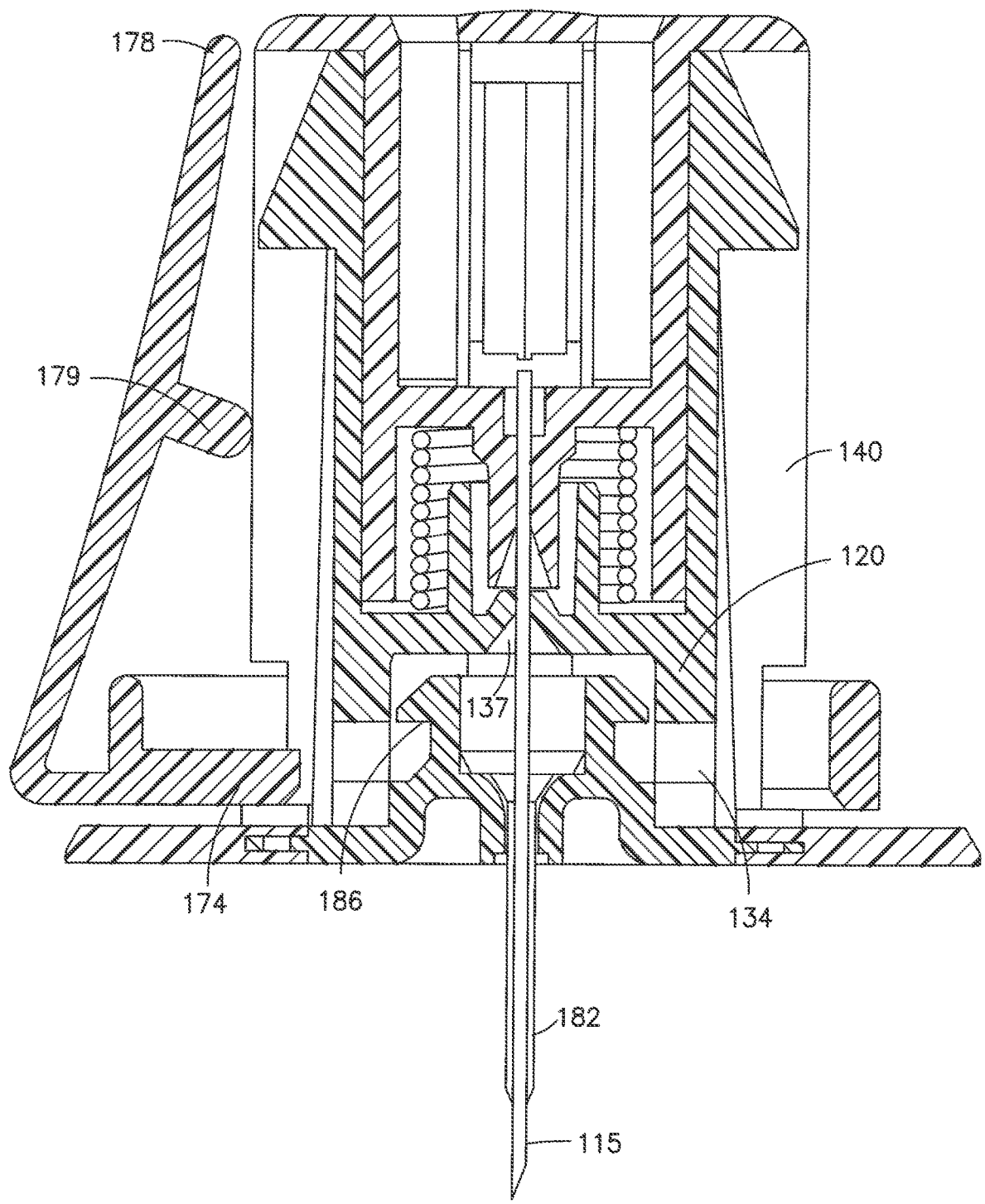
FIG. 12 is a cross-sectional view of the needle tip shield of FIG. 8 in the second operational state and the base of FIG. 8.

FIG. 10 illustrates how the push tab 178 moves to the right to unlock the needle shield 120 and needle hub 140 from the infusion set base 180. Preferably, as a user presses the push tab 178, a force is imparted on the needle hub 140 at the fulcrum 179. As shown in FIG. 11, with the force of the push tab 178 applied to the right, motion is initiated on the lower portion 177 of the lever 175 to the left. FIG. 12 illustrates the actuation button 170 in a second state subsequent to actuation. In the second state, a latch 174 of the actuation button 170 is disengaged from an undercut 186 of the infusion set base 180 and a distal aperture 134 of the needle shield 120.

Once the latch 174 is removed from the distal aperture 134 of the needle shield 120, the spring 156 displaces the needle hub 140 proximally relative to the needle shield 120. The needle shield 120 remains stationary relative to the base 180. Driven by the spring 156, the needle hub 140 and the needle shield 120 continue to move apart from one another until a proximal protrusion 127 on the needle shield 120 engages an inner part of a distal portion 164 and a locking latch 129 disposed on the needle shield 120 locks the needle hub 140 and needle shield 120 in a shielded state (see FIGS. 13-15). After the button 170 is actuated, the needle shield 120 can be removed from a head 184 of the infusion set base 180 (see, e.g., FIG. 13).

Figure 13:
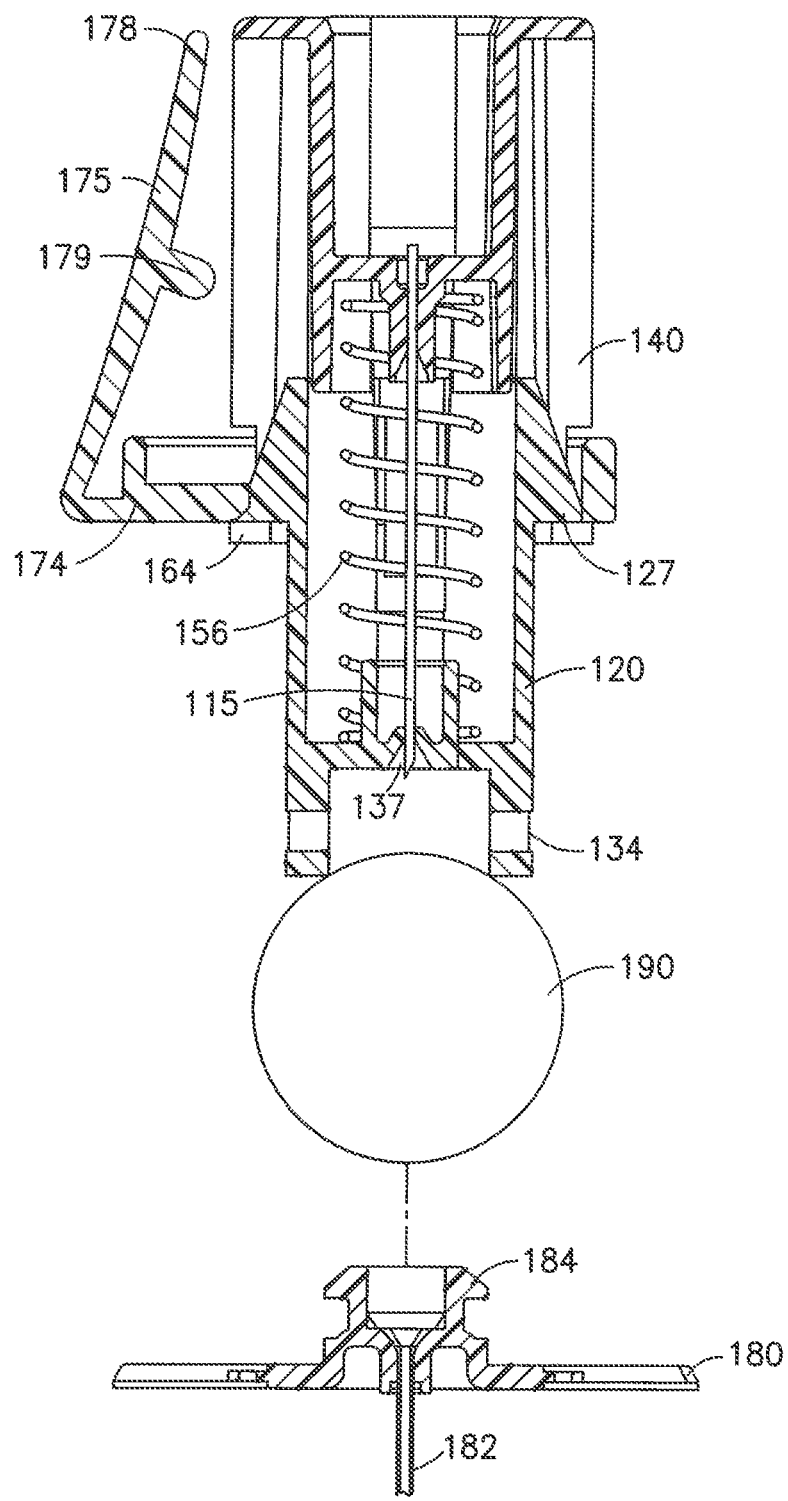
FIG. 13 is a cross-sectional view of the needle tip shield of FIG. 8 in a fully deployed state removed from the base of FIG. 8.
Figure 14:
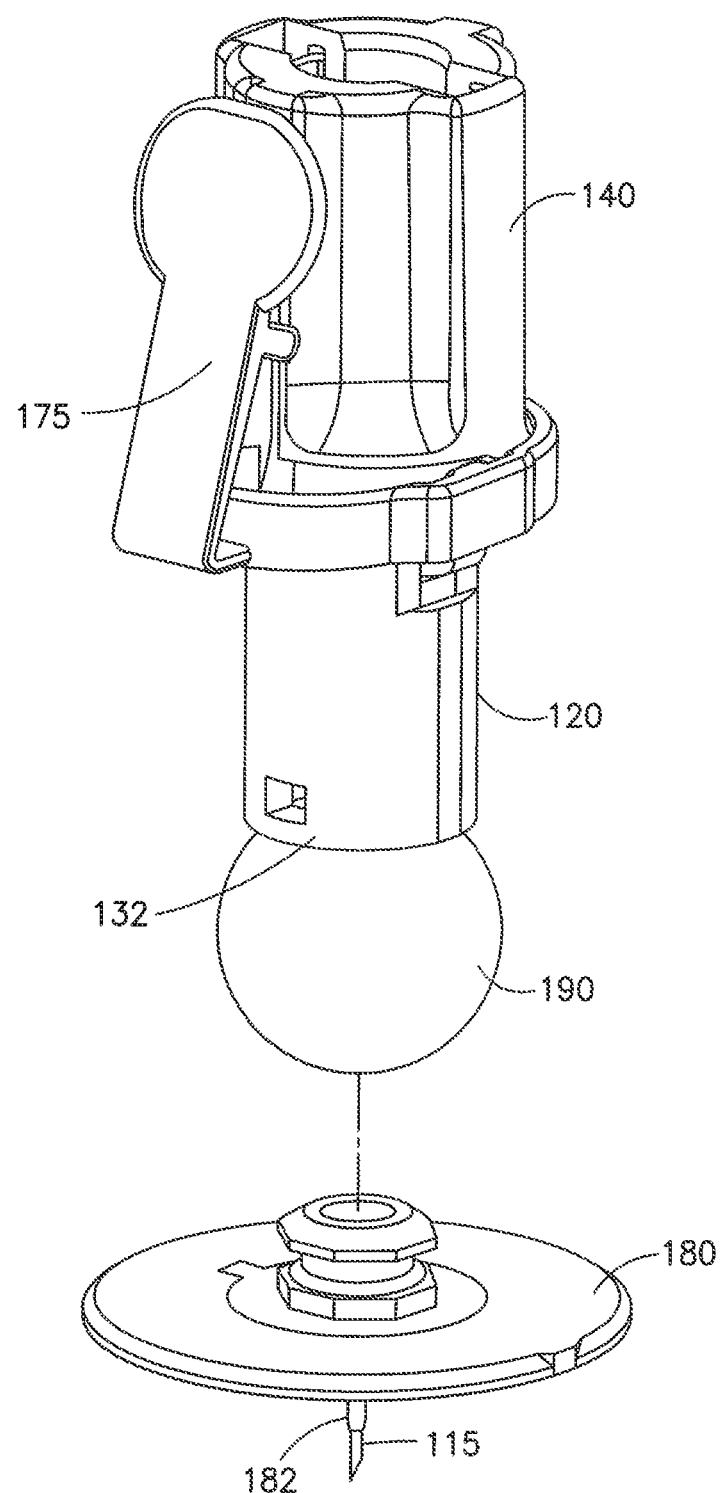
FIG. 14 is a perspective view of the needle tip shield of FIG. 8 in a fully deployed state removed from the base of FIG. 8.
Figure 15:
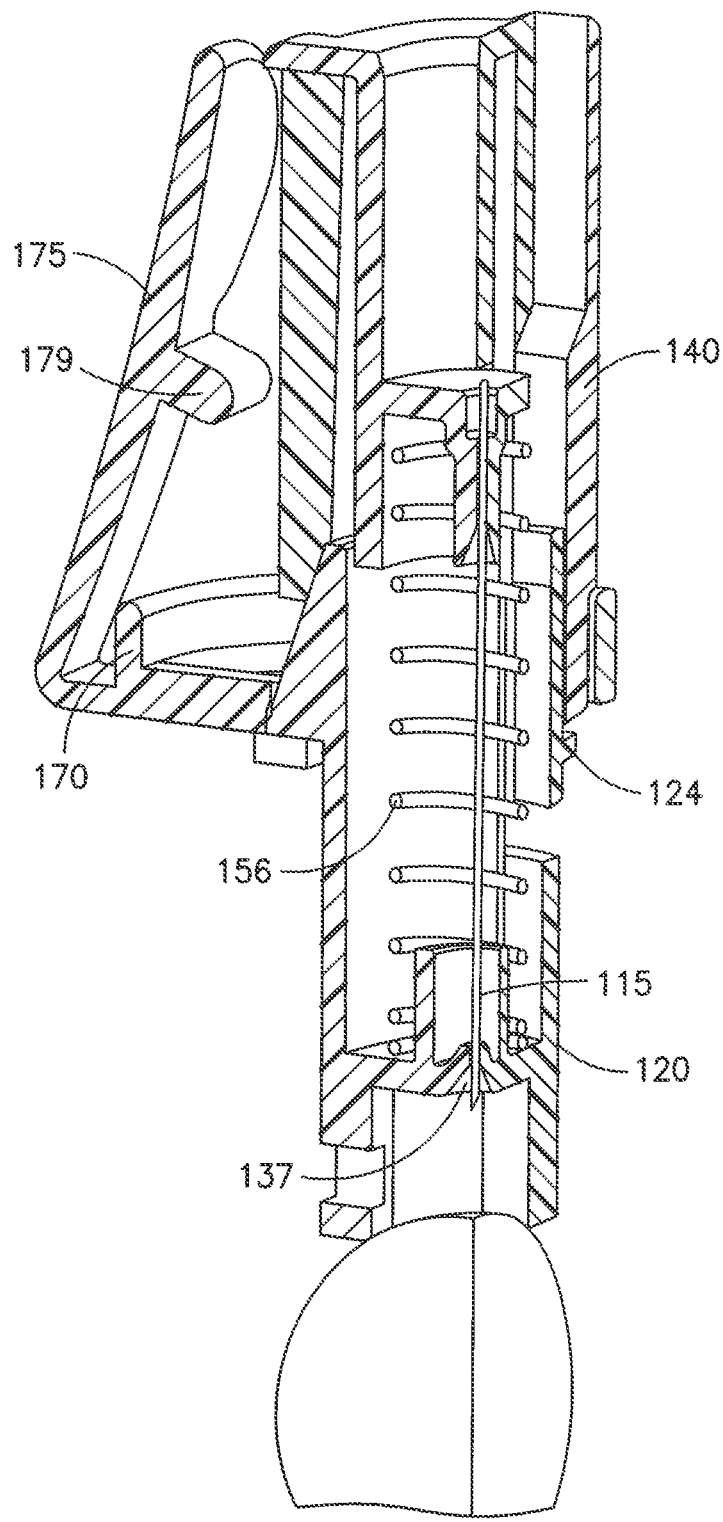
FIG. 15 is a cross-section view of the needle tip shield and the base of FIG. 11 in the fully deployed operational state

FIGS. 13 and 14 illustrate the state in which the needle hub 140 has fully displaced relative to the needle shield 120. The introducer needle 115 is drawn out of the catheter 182 and into the needle shield opening 137. The needle shield 120 surrounds and conceals the introducer needle 115 so that an average finger represented by sphere 190 will not fit through the distal opening 132 of the needle shield. Therefore, a user is provided with a mechanism to protect from an accidental needle stick.

It will be appreciated by those skilled in the art that changes may be made to the embodiments described herein without departing from the scope of the invention. It is particularly noted that the features of different embodiments and claims may be combined with each other as long as they do not contradict each other. All such changes and combinations are considered to be within the scope of the invention, which is defined by the appended claims and their equivalents.

The invention claimed is:

1. A needle assembly, comprising:
a needle having a sharpened end and an opposing end; and
a needle tip shield for shielding the needle, comprising:
   a needle shield; and
   a needle hub fixedly connected to the opposing end of the needle, wherein the needle shield and the needle hub are displaceable relative to each other from a first state, in which the sharpened end of the needle is exposed outside the needle shield, to a second state, in which the sharpened end of the needle is shielded by the needle shield; and
   an actuation button disposed on the needle hub, movable with the needle hub from the first state to the second state, and movable transversely relative to the needle hub, the actuation button maintaining the needle shield and the needle hub in a releasable locked state in a first button position relative to the needle hub and permitting the needle shield and the needle hub to displace relative to each other in a second button position relative to the needle hub
wherein the actuation button includes:
   a user interface disposed on a first external side of the needle hub; and
   a latch extending radially inward through an aperture on a second, opposing external side of the needle hub and through an aperture of the needle shield in the first button position.

2. The needle assembly according to claim 1, wherein the actuation button is disposed on an outer wall of the needle hub.

3. The needle assembly of claim 1, wherein:
the needle hub includes an inner wall and an outer wall connected at a proximal end of the needle hub and the needle shield is disposed in an area between the inner wall and the outer wall; and
the needle tip shield further comprises a spring element disposed between the needle hub and the needle shield, wherein upon displacement of the actuation button relative to the needle hub, the spring element displaces the needle hub and the needle shield to the second state.

4. The needle assembly according to claim 1, wherein the actuation button includes a lever extending therefrom for receiving motion from a user to advance the actuation button from the first button position to the second button position.

5. A needle assembly, comprising:
a needle having a sharpened end and an opposing end; and
a needle tip shield for shielding the needle, comprising:
   a needle shield connectable to a base; and
   a needle hub fixedly connected to the opposing end of the needle, wherein the needle shield and the needle hub are displaceable relative to each other from a first state, in which the sharpened end of the needle is exposed outside the needle shield, to a second state, in which the sharpened end of the needle is shielded by the needle shield; and
   an actuation button movably connected to the needle hub to maintain the needle shield and the needle hub in a releasable locked state in a first button position relative to the needle hub and to permit the needle shield and the needle hub to displace relative to each other in a second button position relative to the needle hub;
wherein the needle shield and the needle hub each have an aperture for receiving the actuation button in the first state; and
the needle assembly further comprises the base, wherein the base includes a column extending therefrom and a head extending from the column forming an undercut between the base and the head, and wherein the actuation button extends through the apertures of the needle shield and the needle hub and engages the undercut to releasably lock the needle shield and the needle hub together and releasably engage the needle shield and the needle hub with the base.

6. The needle assembly of claim 5, wherein the actuation button includes a lower latch that engages the undercut to releasably engage the needle shield and the needle hub with the base.

7. A needle assembly, comprising:
a needle having a sharpened end and an opposing end, the needle being insertable through a base; and
a needle tip shield, comprising:
  a needle hub arranged to releasably engage with the base, the needle hub being fixedly connected to the opposing end of the needle and having an inner recess;
  an actuation button disposed on an outer wall of the needle hub;
  a needle shield, having a distal shield aperture, movably disposed in the inner recess, wherein in a first state of the needle shield relative to the needle hub, in which the sharpened end of the needle is exposed outside the needle shield, the actuation button extends through a transverse aperture of the needle shield and a transverse aperture of the needle hub, and is arranged to engage the base to releasably lock the needle shield and the needle hub together and releasably engage the needle shield and the needle hub with the base; and
  a biasing element biasing the needle hub and the needle shield axially apart;
  wherein displacement of the actuation button relative to the needle hub is configured to release the needle hub and the needle shield from the base and release the biasing element; and
  wherein the needle shield displaces relative to the needle hub to cover the sharpened end of the needle.

8. The needle assembly according to claim 7, wherein the actuation button includes a lever extending therefrom for receiving motion from a user to advance the actuation button from the first state to the second state.

9. The needle assembly according to claim 8, wherein the lever includes a push tab configured to be actuated by a user and a fulcrum for imparting a force on the needle hub to initiate motion of the actuation button.

10. The needle assembly according to claim 7, wherein the needle hub displaces along with the actuation button relative to the needle shield to cover the sharpened end of the needle.

11. A needle assembly for an infusion set, comprising:
a needle having a sharpened end and an opposing end; and
a needle tip shield for shielding the needle, comprising:
  a needle shield connectable to an infusion set base;
  a needle hub fixedly connected to the opposing end of the needle, wherein the needle shield and the needle hub are displaceable relative to each other from a first state, in which the sharpened end of the needle is exposed outside the needle shield, to a second state, in which the sharpened end of the needle is shielded by the needle shield; and
  an actuation button connected to the needle hub and movable from a first button position relative to the needle hub to a second button position relative to the needle hub;
  wherein the needle hub includes ratchet teeth on an outer wall thereof; and
  includes a pawl structure on a surface thereof that engages with the ratchet teeth and maintains connection of the actuation button with the needle hub.

12. The needle assembly of claim 11, wherein the needle shield and the needle hub each have an aperture for receiving the actuation button in the first state.

13. The needle assembly of claim 11, wherein the actuation button includes a latch to releasably engage the needle shield and the needle hub with the infusion set base.

14. The needle assembly of claim 11, wherein:
the needle hub includes an inner wall and an outer wall connected at a proximal end of the needle hub and the needle shield is disposed in a recess between the inner wall and the outer wall; and
the needle tip shield further comprises a spring element disposed between the needle hub and the needle shield, wherein upon displacement of the actuation button relative to the needle hub from the first button position to the second button position, the spring displaces the needle hub and the needle shield to the second state.

15. The needle assembly according to claim 11, wherein the actuation button includes a lever extending therefrom for receiving motion from a user to advance the actuation button from the first state to the second state.

16. The needle assembly of claim 11, wherein:
the needle hub includes:
an inner wall connected to the outer wall at a proximal end of the needle hub; and
a hub shelf extending radially inside the inner wall;
the needle shield includes a shield shelf extending radially inward; and
the needle assembly further includes a spring disposed between the hub shelf and the shield shelf.

* * * * *